(12) United States Patent
Hayford et al.

(10) Patent No.: US 7,047,819 B2
(45) Date of Patent: May 23, 2006

(54) TESTING OF SAMPLES

(75) Inventors: Paul D. Hayford, High Wycombe (GB); David W. Long, Tring (GB)

(73) Assignee: Instron Limited (GB)

( * ) Notice: Subject to any disclaimer, the term of this patent is extended or adjusted under 35 U.S.C. 154(b) by 0 days.

(21) Appl. No.: 10/683,072

(22) Filed: Oct. 10, 2003

(65) Prior Publication Data
US 2004/0145724 A1 Jul. 29, 2004

(30) Foreign Application Priority Data
Oct. 10, 2002 (GB) ................................. 0223607.3
Oct. 17, 2002 (GB) ................................. 0224205.5

(51) Int. Cl.
*G01L 1/24* (2006.01)
(52) U.S. Cl. ....................................................... 73/800
(58) Field of Classification Search .................. 73/797,
73/800, 23.36, 788, 809, 808, 841–845, 81;
356/32, 33, 35.5; 374/165
See application file for complete search history.

(56) References Cited

U.S. PATENT DOCUMENTS

| | | | | |
|---|---|---|---|---|
| 3,715,915 A | * | 2/1973 | Williams | 73/800 |
| 3,937,071 A | * | 2/1976 | Slota et al. | 73/809 |
| 4,286,843 A | * | 9/1981 | Reytblatt | 359/489 |
| 4,690,552 A | * | 9/1987 | Grant et al. | 356/35.5 |
| 5,029,194 A | * | 7/1991 | Young et al. | 378/89 |
| 5,361,641 A | | 11/1994 | Eldridge et al. | 73/842 |
| 5,659,140 A | * | 8/1997 | Jakob et al. | 73/788 |
| 5,683,181 A | * | 11/1997 | Shepard | 374/165 |
| 5,913,246 A | * | 6/1999 | Simonelli et al. | 73/808 |
| 6,023,980 A | * | 2/2000 | Owen et al. | 73/797 |

FOREIGN PATENT DOCUMENTS

| | | |
|---|---|---|
| EP | 0 374 735 B1 | 6/1990 |
| GB | 2 205 396 A | 12/1988 |
| GB | 2 223 319 A | 4/1990 |

* cited by examiner

*Primary Examiner*—Max Noori
*Assistant Examiner*—Octavia Davis
(74) *Attorney, Agent, or Firm*—Renner, Kenner, Greive, Bobak, Taylor & Weber

(57) ABSTRACT

Test apparatus comprising means for holding a sample to be tested, means for altering the strain in the sample, an optical arrangement for monitoring the sample to be tested, and processing means for processing the signals resulting from the monitoring of the sample under test, wherein the environment between the optical arrangement and the sample under test is controlled, and wherein the sample to be tested is located in a position external to the controlled environment.

7 Claims, 2 Drawing Sheets

TESTING OF SAMPLES

Figure 1:
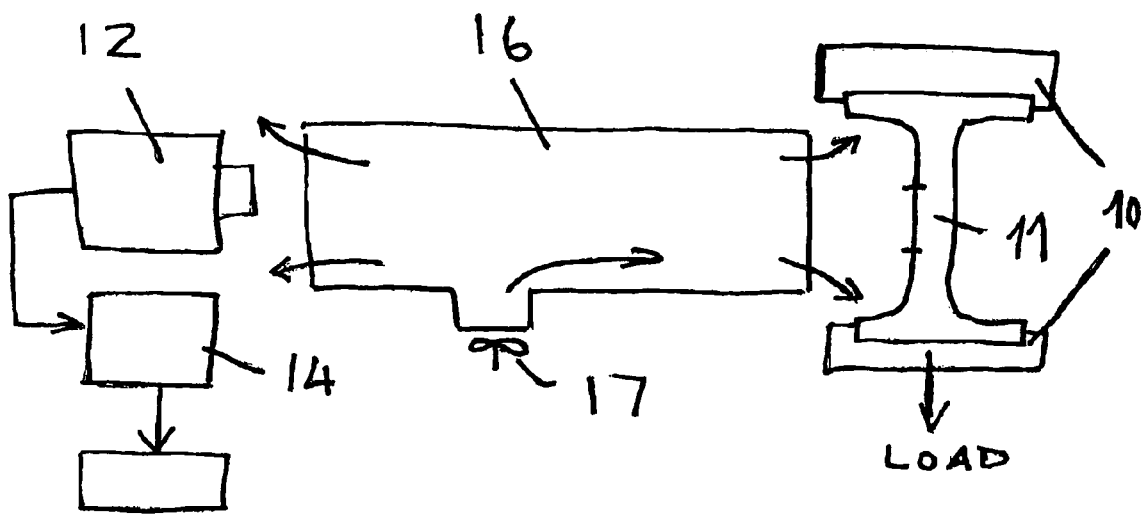

The present invention relates to the testing of samples and more particularly to the mechanical testing of materials, or of components.

It is common when testing materials to undertake tensile tests of materials by forming a standard sample, marking the sample with one or more datum points and applying an increasing load to the sample while monitoring movement of the datum point or points. It is known to utilise video cameras for the purposes of monitoring the movement and by using a suitable mathematical algorithm, the distance between the marks can be determined. This technique results in an apparatus which is reliable and cost effective. However, there is a demand for more accurate measurement techniques which can currently only be satisfied with expensive equipment.

Two prior disclosures, GB 2205396A and GB 2223319A, are both relevant in describing the technology which already exists in the field of the present invention. Both these documents describe an arrangement wherein the sample to be tested is contained in an environmentally controlled test chamber and viewed through a transparent window. As the sample is located within the test chamber, problems may exist due to the need to view the sample through a window and further the environment between the camera and the window is different to the environment within the test chamber, which leads to possible inaccuracy.

It is an object of the present invention to improve the accuracy of the existing apparatus such as is used generally in the art and which does not require the sample to be located in a spherical test chamber.

The present invention provides testing apparatus comprising means for holding a sample to be tested, means for altering the strain in the sample to be tested, an optical arrangement for monitoring the sample to be tested, and processing means for processing the signals resulting from the monitoring of the sample under test characterised in that the environment between the optical arrangement and the sample under test is controlled.

The optical arrangement preferably includes a camera and an advantage of the present invention is that the area between the camera and the sample is subjected to uniform conditions.

Preferably, a characteristic of the atmosphere in the space between the camera and the sample is controlled. The characteristic is preferably the density of the air but may additionally or alternatively be the temperature, humidity or other characteristic which will adversely affect the accuracy of the signals resulting from the monitoring.

In the preferred embodiment, the control of the environment between the camera and the sample under test is achieved by inducing a controlled flow of air in the said region. Preferably, the air is processed so that its refractive index in the region is constant which is a result of the air in the controlled environment having a constant density.

Figure 2:
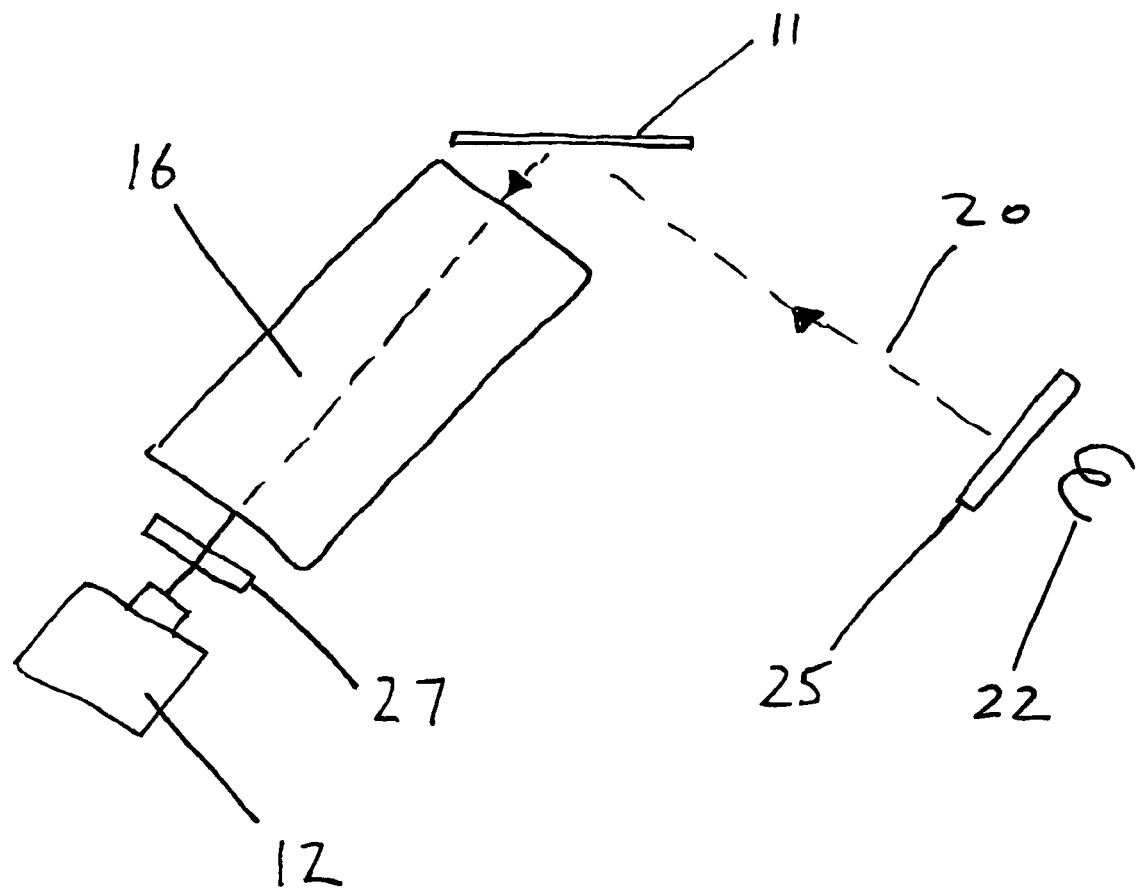

In order that the present invention be more readily understood, an embodiment thereof will now be described by way of example only with reference to the accompanying drawings in which:

FIG. 1 shows a diagrammatic representation of a preferred embodiment of the apparatus according to the present invention; and FIG. 2 shows a plan view of an alternative embodiment of the apparatus according to the present invention.

The preferred embodiment will be described in relation to its use as a test apparatus for tensile testing a metal sample but it will be appreciated that the material of the sample is not significant and any suitable material or component can be tested. Additionally, compression or shear testing could be undertaken rather than tensile testing.

Referring to FIG. 1, the test apparatus comprises the basic components of a sample holder 10 for holding a sample 11 of the material to be tested which sample is provided with marks in the usual fashion. The sample holder is conventional and is arranged to enable varying loads to be placed on the sample under test in a manner which is not shown but is conventional in the art. The sample 11 under test is monitored by an optical arrangement in the form of a camera 12 which in this case is a video camera. Video cameras are useful because of their high effective shutter speed but it will be appreciated that a still camera could equally well be used if desired. It is preferred to utilise digital cameras.

The output from the camera is fed to a signal processing computer (14) where an algorithm is used to determine the mark separation and to produce the results for the sample under test which are output in any convenient form.

We have found that the accuracy now required of the apparatus is such that the accuracy of the measurements was being affected by the properties of the environment in the space between the camera and the sample under test. For this reason, the present embodiment controls one or more characteristics of the environment in the region between the camera and the sample. Rather than attempting to control the whole of the environment containing the camera and the sample under test, the present embodiment defines a restricted volume of the overall environment and seeks to closely control the characteristics of this restricted volume. In the present embodiment this is principally achieved by use of a tubular member whose axis is aligned with the optical axis of the camera and extending therebetween. We have found that one important characteristic is the density of the air which should be maintained constant and uniform in order to control the refractive index of the air. This is most conveniently achieved by providing a tube 16 through which the camera 12 views the sample 11 under test. The tube 16 is supplied with ambient air via one or more fans 17 and one or more filters for removing dust from the air which results in the atmosphere in the tube 16 having uniform characteristics throughout the length of the tube. Further, the tube 16 defines a volume dependent on the shape of the tube and is open-ended so as to permit air flow out of one or both ends of the tube. The sample itself may be located in a larger uncontrolled environment with the tube representing a relatively smaller controlled environment. The fan 17 produces homogeneously mixed air to the interior of the tube at a pressure above atmospheric pressure sufficient to promote mixing and flow. It is not necessary to seal the ends of the tube in view of the fact that air flows out of the tube and so has the effect of sweeping away any ambient air from the front of the camera and the sample.

The location and orientation of the fan 17 is not critical. As shown, the fan 17 directs air at an angle into the tube 16. It is equally possible to have one or more fans fitted to the tube 16 adjacent the camera 12 so as to blow air axially along the length of the tube. Further, it is possible to adjust any other aspect of the fan so as to achieve the desired air flow within the controlled environment. For example, the position, angle and/or number of fans may be adjusted to achieve the desired effect. Accordingly, the positioning of the fan is not restricted to that shown in the Figure.

Likewise, the cross-sectional shape of the tube 16 is not critical eg the cross-section may be oval or rectangular with the long axis parallel to the length dimension of the sample 11. Also, the tube need not be of constant cross-section throughout its length. It may be of rectangular cross-section with the area of the cross-section increasing with distance from the camera 12. Preferably the increase is linear. Further, the tapering of the tube 16 may be such as to match the beam spread of the camera 12. Thus, to match the beam spread of the camera 12 as positioned in the FIG. 1, the tube 16 would taper towards the camera and hence the area of the cross-section would increase with distance from the camera.

Using the above apparatus, we have found that by utilising a video camera having a CCD array with approximately 1000 lines and a field of view of 100 mm, the accuracy of the apparatus can be improved so that the separation between two datum points (marks) in a sample under test can be measured within a resolution of ±1 µm. Even if a high resolution CCD and optics are used in an attempt to improve accuracy, we have found that noise due to variations in the atmospheric conditions cause distortion of the light to such an extent that the full benefit of upgrading the quality of the camera and optics is not achieved. A possible modification to the monitoring of the sample will now be described in detail by referring to FIG. 2.

When monitoring movement of the marked areas of the samples, it is important that there is adequate contrast between the marked areas of the sample and the background sample surface for the video camera to form accurate clearly defined boundaries between the spots and the surrounding surface. However, the surface on which the marks are applied is often specular which tends to reduce the contrast between the marks and the surrounding surface. Accordingly, the preferred embodiment may be altered to address this problem through the use of polarising filters.

Preferably, the monitoring includes illuminating the sample surface with light 20 which has been polarised in a first direction. The light 20 is preferably provided by a light source 22 whose output is passed through a first polarising filter 25 having a first direction of polarization.

The polarised light impinging on the sample surface and marked area is reflected and in the normal course of events, light polarised in the first direction would be reflected from the surface of sample 11 and received by the video camera 12. However, to increase the contrast, the apparatus includes a second polarising filter 27 disposed in front of the video camera 12 and oriented so that its direction of polarization is at 90° to that of the first polarising filter 25. The effect of this is that any polarised light reflected from the sample surface is prevented by the polarising filter 27 from reaching the video camera 12. This in turn means that only diffuse reflected light from the marks is received by the camera 12 and hence the marks appear to the camera relatively bright against a black background. Such an image can be readily processed in the signal processing computer 14 (not shown in FIG. 2).

It should be noted that because the optical arrangement is looking for diffuse reflected light, the optical arrangement need not be accurately placed on the optical axis of light reflected from the surface of sample 11 in order to function properly.

It will be appreciated that various modifications may be made to the apparatus. For example, the fan and dust filter can be replaced by a source of purified air such as from a pressure cylinder. This might require a baffle of some sort to ensure a constant, even flow. It is also conceivable that an air line fitted with appropriate air flow conditioning apparatus might be used.

It should be noted that the aforementioned polarising effect could also be considered separately to the testing apparatus of the present invention and thus is not restricted to operating with the present invention.

A further modification can be made to the alignment of the fan 17 with respect to the tube 16 depending on the construction of the tube 16. For example, when a tapered tube is utilised, the angle of the fan 17 may be adjusted to alter the air flow in different sections of the tube so as to maintain the uniform characteristics of the air throughout the length of the tube and to get an appropriate spread of air in the tube 16.

Also, although the above description assumes visible light, light of other wavelengths such as ultra-violet or infra-red can be used as can laser light.

Although we refer to marks being applied, inherently visible features of the surface can be used instead or indeed an optical image can be used within which image locations can be identified and monitored.

What is claimed is:

1. Test apparatus comprising means for holding a sample to be tested, means for altering the strain in the sample, an optical arrangement for monitoring the sample to be tested, the optical arrangement being spaced from the sample to be tested by a distance, wherein the distance is occupied by a hollow member having air therein, the characteristics of the air being controlled throughout the distance within the hollow member.

2. Apparatus according to claim 1, wherein the optical arrangement includes a camera, and wherein the hollow member is in the form of tube, the camera viewing the sample to be tested through the hollow member.

3. Apparatus according to claim 1, wherein the test apparatus further comprises means for supplying air of constant density into the hollow member.

4. Apparatus according to claim 3, wherein the means for supplying air of constant density comprises one or more fans for providing homogeneously mixed air.

5. Apparatus according to claim 1, wherein the optical arrangement includes a camera, and the output of the camera is processed to produce results of the test.

6. Apparatus according to claim 1, further comprising a means for illuminating the sample to be tested with polarised light polarised in a first direction, and
 a filtering means arranged to prevent polarised light in the first direction being received by the camera, whereby only diffused light will be received.

7. Test apparatus comprising means for holding a sample to be tested, means for altering the strain in the sample, an optical arrangement for monitoring the sample to be tested, wherein the optical arrangement is spaced from the holding means by a distance occupied by air, and hollow means for controlling the characteristics of the air throughout the distance.

* * * * *